(12) United States Patent
Haynes et al.

(10) Patent No.: US 11,701,214 B2
(45) Date of Patent: Jul. 18, 2023

(54) PROSTHETIC HEART VALVE PACKAGING AND ATTACHMENT ASSEMBLY

(71) Applicant: Cephea Valve Technologies, Inc., Santa Clara, CA (US)

(72) Inventors: Evelyn Haynes, Soquel, CA (US); Jonathan Oakden, Santa Cruz, CA (US); Spencer Noe, San Miguel, CA (US); Aaron Grogan, Scotts Valley, CA (US); David Wang, Santa Clara, CA (US)

(73) Assignee: Cephea Valve Technologies, Inc., Santa Clara, CA (US)

( * ) Notice: Subject to any disclaimer, the term of this patent is extended or adjusted under 35 U.S.C. 154(b) by 315 days.

(21) Appl. No.: 17/317,377

(22) Filed: May 11, 2021

(65) Prior Publication Data

US 2021/0361404 A1 Nov. 25, 2021

Related U.S. Application Data

(60) Provisional application No. 63/028,716, filed on May 22, 2020.

(51) Int. Cl.
*A61F 2/00* (2006.01)
*A61F 2/24* (2006.01)

(52) U.S. Cl.
CPC .......... *A61F 2/0095* (2013.01); *A61F 2/2409* (2013.01); *A61F 2/2427* (2013.01); *A61F 2220/0075* (2013.01)

(58) Field of Classification Search
CPC .... A61F 2/0095; A61F 2/2409; A61F 2/2427; A61F 2220/0075

USPC ......................................................... 206/438
See application file for complete search history.

(56) References Cited

U.S. PATENT DOCUMENTS

| | | | |
|---|---|---|---|
| 5,720,391 A * | 2/1998 | Dohm | A61F 2/0095 206/583 |
| 10,470,881 B2 | 11/2019 | Noe et al. | |
| 2012/0046738 A1 | 2/2012 | Lau | |
| 2018/0028177 A1 | 2/2018 | van Oepen et al. | |
| 2018/0028305 A1 | 2/2018 | von Oepen et al. | |
| 2018/0028779 A1 | 2/2018 | von Oepen et al. | |
| 2018/0028787 A1 | 2/2018 | McNiven et al. | |
| 2018/0055636 A1 | 3/2018 | Valencia et al. | |
| 2018/0055637 A1 | 3/2018 | von Oepen et al. | |
| 2018/0056033 A1 | 3/2018 | von Oepen et al. | |
| 2018/0056043 A1 | 3/2018 | von Oepen et al. | |
| 2018/0092744 A1 | 4/2018 | von Oepen et al. | |
| 2018/0126095 A1 | 5/2018 | von Oepen et al. | |

(Continued)

*Primary Examiner* — Jacob K Ackun
(74) *Attorney, Agent, or Firm* — Sleman & Lund LLP (57) ABSTRACT

A system for heart valve repair includes a packaging assembly for storing the replacement heart valve. The packaging assembly includes a valve support having a base for holding the replacement heart valve, a ring positioned within the valve support and configured to fit around a circumference of the replacement heart valve, and a retention mechanism. The retention mechanism includes a cap and plurality of sutures configured to be attached to the cap and to the replacement heart. The packaging assembly having a locked configuration in which the ring and the valve support are locked together and the sutures tension the replacement heart valve. The packaging assembly is designed to hold and transport a replacement heart valve and fits within a shipment jar.

20 Claims, 12 Drawing Sheets

(56) References Cited

U.S. PATENT DOCUMENTS

| | | | |
|---|---|---|---|
| 2018/0126119 A1 | 5/2018 | McNiven et al. | |
| 2018/0133454 A1 | 5/2018 | von Oepen et al. | |
| 2018/0140411 A1* | 5/2018 | Panus | A61F 2/2412 |
| 2018/0311041 A1* | 11/2018 | Bordoloi | A61F 2/2439 |
| 2019/0328520 A1* | 10/2019 | Kaleta | A61F 2/2409 |
| 2021/0212822 A1* | 7/2021 | Reed | A61F 2/2436 |

* cited by examiner

PROSTHETIC HEART VALVE PACKAGING AND ATTACHMENT ASSEMBLY

CROSS-REFERENCE TO RELATED APPLICATIONS

This application claims the benefit of the filing date of U.S. Provisional Patent Application No. 63/028,716 filed May 22, 2020, the disclosure of which is hereby incorporated herein by reference.

BACKGROUND OF THE DISCLOSURE

A primary treatment for heart valve disease is valve replacement. One form of replacement device is a bioprosthetic replacement valve. Following manufacture of the valve and prior to implantation, the replacement heart valve is packaged and transported to the site of use. Typically, replacement heart valves are packaged in liquid-filled jars. The replacement heart valve preferably is held stationary relative to the jar and submerged in the liquid to prevent or minimize damage to the replacement heart valve.

Prior to implantation, the replacement heart valve is removed from the jar and rinsed to remove the shipment fluid. The replacement heart valve is coupled to a delivery system for placement in the patient. However, rinsing and attaching the replacement heart valve to the delivery system are performed by a practitioner which requires skill and time and can lead to human error.

BRIEF SUMMARY OF THE DISCLOSURE

A first aspect of the disclosure includes a packaging assembly for packaging a replacement heart valve including a valve support having a base, a ring positioned within the valve support and configured to fit around a circumference of the replacement heart valve, and a retention mechanism including a pin extending through a lumen of the valve support and a plurality of sutures attached to the pin, the plurality of sutures are configured to be attached to the replacement heart valve.

In other embodiments, the packaging assembly may have an unlocked configuration, in which the ring and the valve support are detached, and a locked configuration, in which the ring and the valve support are locked together. In the locked configuration, the ring and the valve support may be rotationally and axially locked to one another. The packaging assembly may transition between the unlocked and locked configurations by rotation of at least one of the ring and the valve support relative to the other. In the locked configuration, the ring and the valve support may be locked together by a snap-fit connection. The retention mechanism may further include a cap attached to the pin for securing the plurality of sutures. The cap may include a plurality of openings, each opening is configured to receive at least one suture. An outer surface of the cap may be threaded for threaded engagement with a delivery system. The ring may include an annular body and at least one locking tab extending radially outward of the body. The valve support may include a ledge projecting radially inward from the base to define a groove for receiving a respective one of the at least one locking tab. The ring may include four locking tabs and the valve support includes four grooves for receiving the locking tabs. Each of the locking tabs may include an extension extending proximally from a proximal surface of the locking tab. A side surface of each extension may be configured to abut a side surface of the ledge to prevent over rotation of the ring. The pin may extend coaxial to a longitudinal axis of the replacement heart valve. The valve support may include a cannulated rod defining the lumen, the cannulated rod extending proximally from the base of the valve support. The valve support may include a plurality of ribs extending distally from the base.

Another aspect of the disclosure includes a system for heart valve repair including a replacement heart valve and a packaging assembly for storing the replacement heart valve. The packaging assembly includes a valve support having a base for holding the replacement heart valve, a ring positioned within the valve support and configured to fit around a circumference of the replacement heart valve, and a retention mechanism including a cap and plurality of sutures configured to be attached to the cap and to the replacement heart. The packaging assembly has a locked configuration in which the ring and the valve support are locked together and the sutures tension the replacement heart valve.

In other embodiments, the cap may include a threaded outer surface for threaded engagement with a delivery system. The replacement heart valve may have an hour glass shape defining a waist, and the ring may be configured to fit securely around the waist. The replacement heart valve may include a plurality of attachment members for receiving the sutures of the retention mechanism. The replacement heart valve may include an anchor assembly having an atrial anchor and a ventricular anchor, the atrial anchor including a plurality of attachment members in the form of pins for receiving the suture of the retention mechanism. The cap of the retention mechanism may include a plurality of openings for receiving the suture, such that the suture extends between a respective one of the plurality of openings of the cap and a respective one of the plurality of attachment members. The ring may include an annular body and at least one locking tab extending radially outward of the body. The valve support may include a ledge projecting radially inward from the base and defining a groove for receiving a respective one of the at least one locking tab. The ring may include four locking tabs and the valve support includes four grooves for receiving the locking tabs. Each of the locking tabs may include an extension extending proximally from a proximal surface of the locking tab. A side surface of each extension may be configured to abut a side surface of the ledge to prevent over rotation of the ring. The retention mechanism may further include a pin, a first end of the pin attached to the valve support and a second end of the pin attached to the cap. The valve support may include a cannulated rod defining a lumen for receiving the pin, the cannulated rod extending proximally from the base of the valve support. The valve support may include a plurality of ribs extending distally from the base.

Another aspect of the present disclosure includes a system for heart valve repair including a packaging assembly for storing a replacement heart valve and a shipment jar for receiving the packaging assembly. The packaging assembly includes a valve support having a base for holding the replacement heart valve, a ring positioned within the valve support and configured to fit around a circumference of the replacement heart valve, and a retention mechanism including a cap and plurality of sutures configured to be attached to the cap and to the replacement heart. The packaging assembly has a locked configuration in which the ring and the valve support are locked together and the sutures tension the replacement heart valve.

DETAILED DESCRIPTION

The packaging assemblies of the present disclosure hold a replacement heart valve securely in a shipment jar container and allow for pre-tensioning of the replacement valve such that the replacement valve is secured and tensioned in the packaging during shipment. The packaging assembly further allows rinsing and attachment to the delivery system to occur while the replacement heart valve is in a protected configuration securely within the packaging assembly.

Figure 1A:
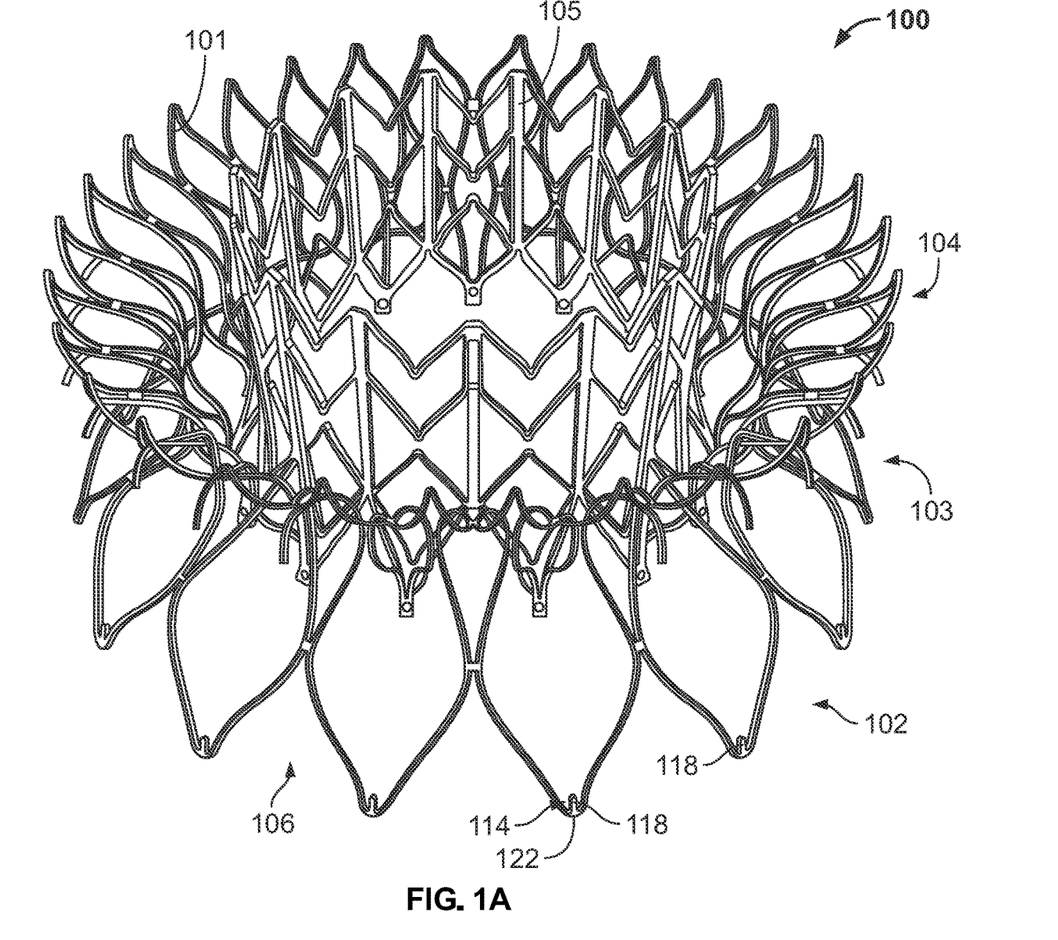
FIGS. 1A and 1B show an illustrative replacement heart valve of the prior art for use in conjunction with the packaging assemblies of the present disclosure.
Figure 1B:
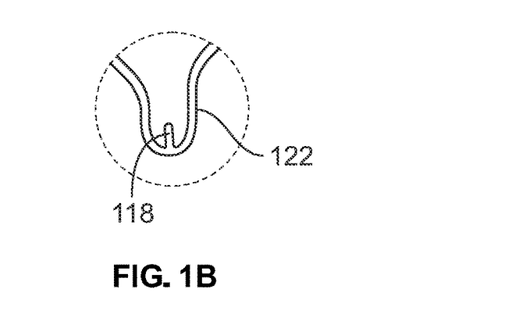

The packaging assemblies of the present disclosure may be used with replacement heart valves, such as replacement heart valve 100, which is an expandable prosthetic implant having an expanded configuration and a collapsed configuration. Replacement heart valve 100 may be a replacement mitral valve having a stent that includes an anchor assembly and a strut frame disposed within the anchor assembly. However, replacement heart valve 100 may be suitable for use in replacing other native heart valves, such as the tricuspid valve, aortic valve, or pulmonary valve, although it may be best suited for replacing the atrioventricular valves. Anchor assembly 101 includes an atrial anchor 102, a ventricular anchor 104 and a central portion 103 positioned axially between the atrial and ventricular anchors. Atrial anchor 102 is configured to be positioned on an atrial side of a mitral valve annulus, and ventricular anchor 104 is configured to be positioned on a ventricular side of the mitral valve annulus. Anchor assembly 101 may have an hour glass shape in that each of the atrial anchor 102 and the ventricular anchor 104 flares radially outward of the central portion 103, such that central portion 103 defines a waist between the atrial anchor 102 and the ventricular anchor 104. Replacement heart valve 100 may also include a strut frame 105 positioned radially inward of anchor assembly 101 and formed of a plurality of connected struts. The radially inner surfaces of strut frame 105 define a perimeter of central opening 106, which allows blood to flow through replacement heart valve 100 in the antegrade direction. Exemplary replacement heart valves are described in U.S. Pat. No. 10,470,881, filed on Feb. 28, 2018 and entitled Replacement Mitral Valves, the disclosure of which is hereby incorporated by reference herein in its entirety.

Replacement heart valve 100 includes one or more prosthetic leaflets (not shown). The leaflets may be secured to an interior of strut frame 105 and may be disposed at least partially in central opening 106. The prosthetic leaflets are configured to coapt with each other in order to control blood flow therethrough, allowing blood to flow in a direction from the atrial anchor 102 toward the ventricular anchor 104 (the antegrade direction), but to substantially block from flowing in the opposite (retrograde) direction. The inner and/or outer surfaces of each of the anchor assembly 101 and the strut frame 105 may be partially or fully covered by cuffs or skirts, including those of fabric and/or tissue materials.

Replacement heart valve 100 includes a delivery device attachment mechanism. For example, at least one atrial tip 114 of atrial anchor 102 forms crest 122 having attachment members 118, such as pins, to which suture loops can be secured, shown in FIGS. 1A and 1B. In the preferred embodiment, replacement heart valve 100 includes a plurality of attachment members 118. These attachment members 118 can be straight hooks, curved hooks, pins, or other structures extending from a strut or member of the valve and to which a suture loop can be securely connected during shipment and subsequent delivery of the valve during surgery. Attachment members 118 are sized and shaped to allow release of the suture loops from the attachment member and thus the valve after deployment of the valve within the patient. Thus, in the illustrated embodiment of FIG. 1B, attachment member 18 is in the form of a pin provided at the apex of each crest 122.

Figure 2:
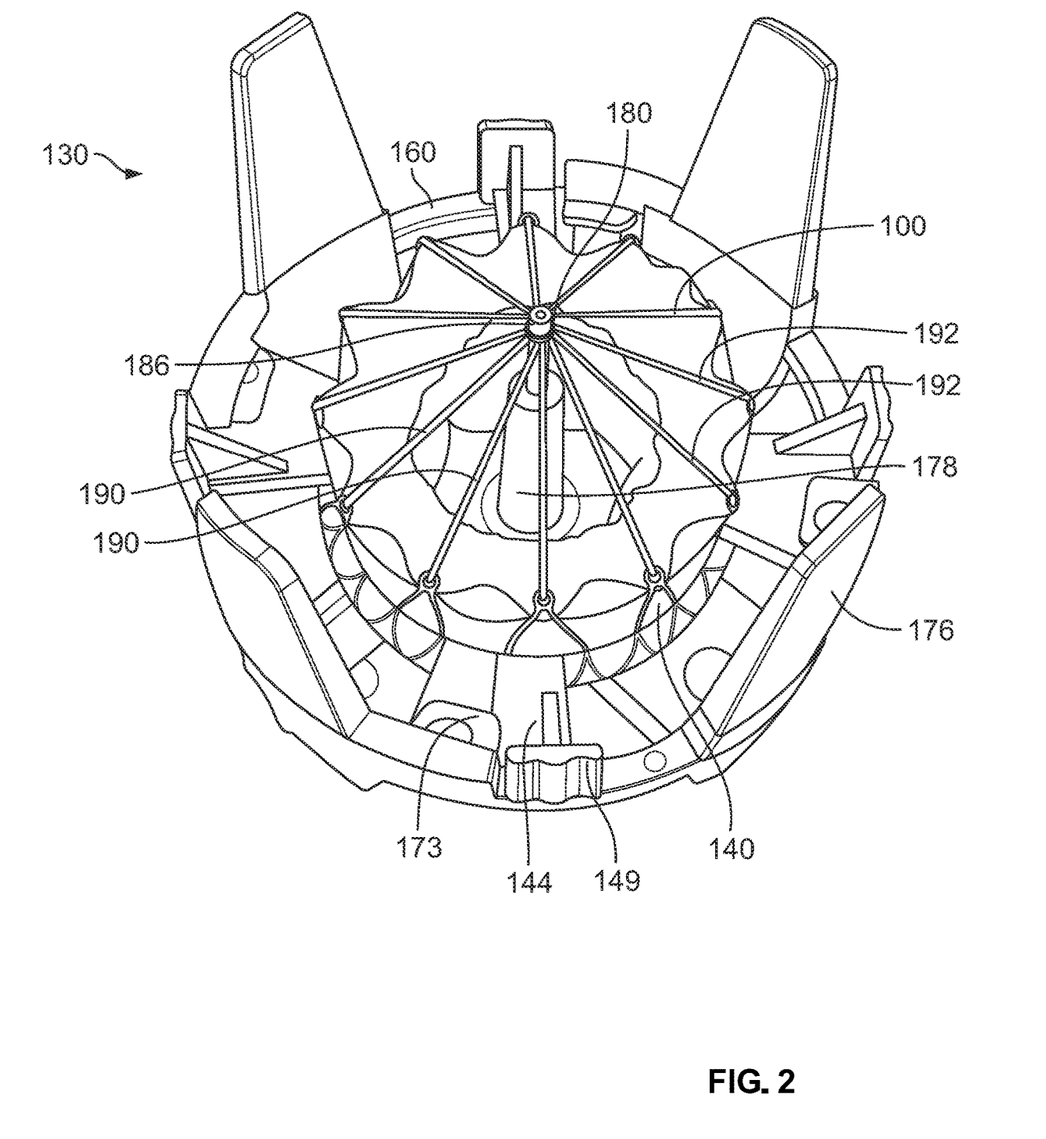
FIGS. 2-3 are photographs of a system for heart valve repair according to an aspect of the present disclosure, the system including a packaging assembly shown in conjunction with the replacement heart valve of FIGS. 1A and 1B.
Figure 3:
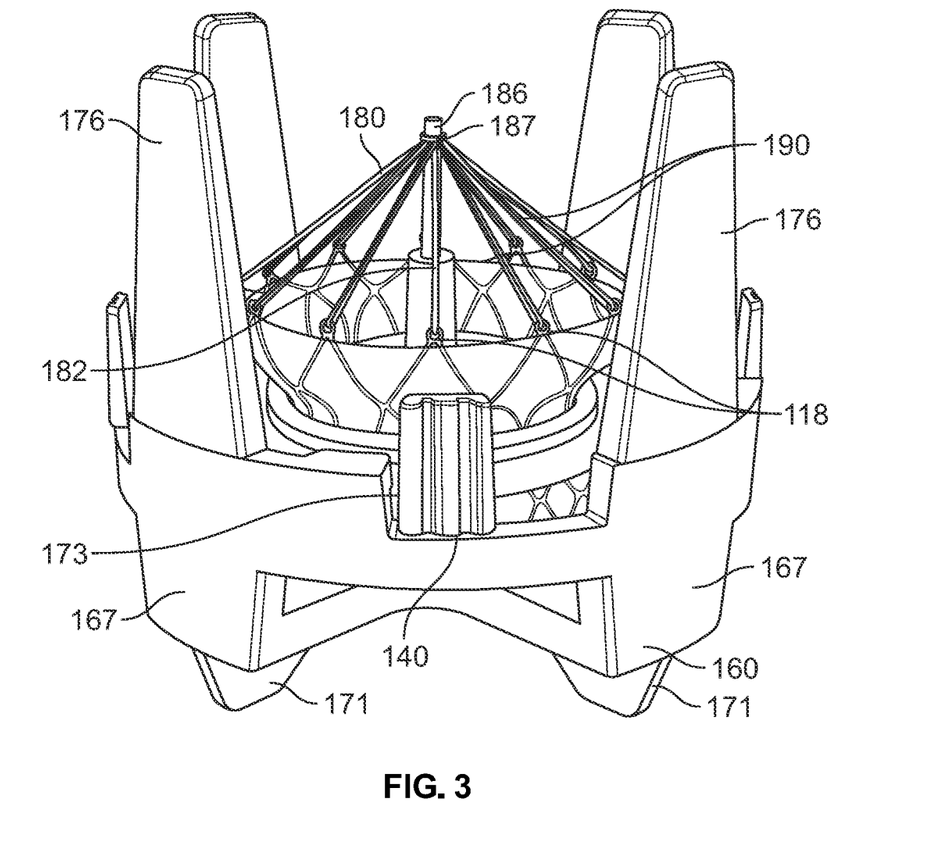
Figure 4:
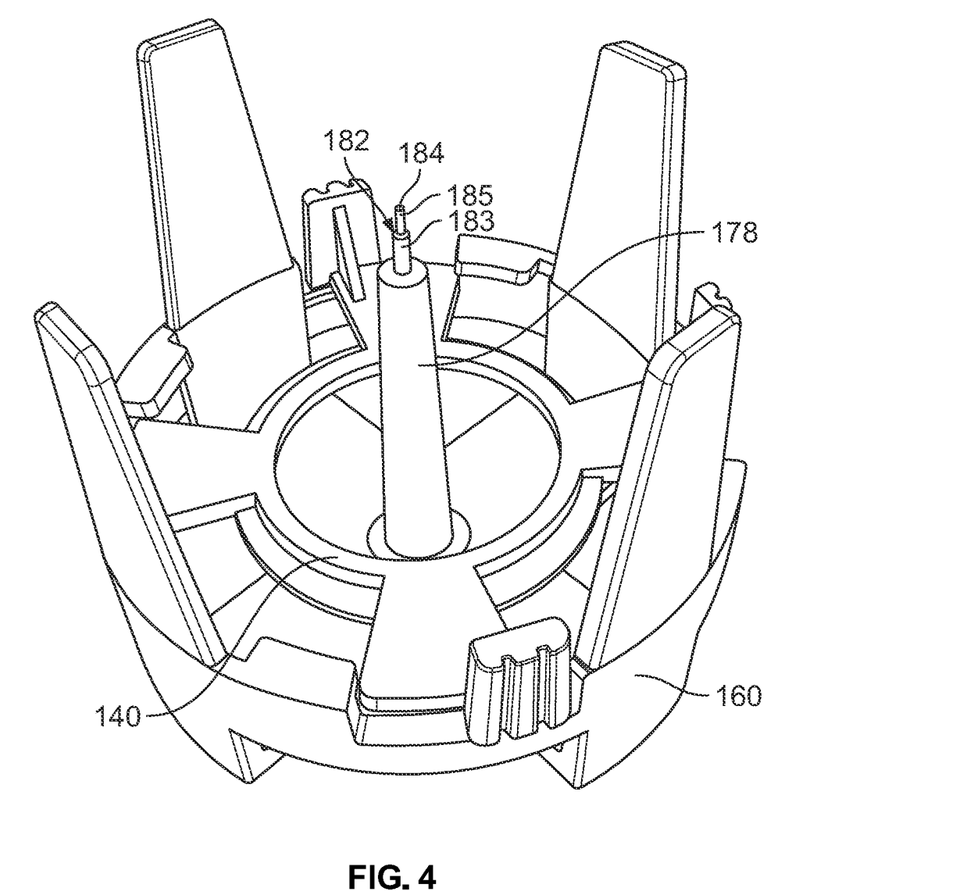
FIG. 4 is a photograph of the packaging assembly of FIGS. 2-3.

FIGS. 2-4 show packaging assembly 130 according to an aspect of the present disclosure in its assembled configuration with replacement heart valve 100 secured within the packaging assembly. In this regard, packaging assembly 130 is designed for use in conjunction with replacement heart valve 100 to form a system for heart valve repair. Packaging assembly 130 includes a ring 140 positioned at least partially within a valve support 160, as shown in FIGS. 2 and 3. Ring 140 and valve support 160 may each be formed via injection molding. Packaging assembly 130 further includes retention mechanism 180 for securely attaching and tensioning the replacement heart valve 100 so that the replacement heart valve is already prepared for attachment to the delivery system while in the packaging, allowing for more efficient implantation. Ring 140 has an inner diameter sized such that the ring fits snugly around central portion 103 of replacement heart valve 100 to prevent the replacement heart valve from shifting when positioned in a final configuration in the packaging assembly 130. In some embodiments, the inner diameter of ring 140 is about equal to, or smaller than, the exterior diameter of the central portion 103 of replacement heart valve 100 while the replacement heart valve is in the expanded condition. Accordingly, ring 140 has a first, outer diameter that is smaller than a second, inner diameter of the valve support 160 to allow the ring to fit within the valve support 160.

Ring 140 may attach to valve support 160 with an attachment mechanism that allows ring 140 to removably attach to valve support 160 such that ring 140 and valve support 160 can be moved from an unlocked configuration in which the two are detached and can rotate relative to one another to a locked configuration in which the ring 140 is rotationally and axially locked to the valve support 160. Generally, valve support 160 forms the holding component of the packaging assembly 130 in which replacement heart valve 100 is securely positioned. Accordingly, valve support 160 defines a second, inner diameter that is greater than the first outer diameter of ring 140 so that the ring 140 can fit within the valve support 160. Further, the height and outer diameter of valve support 160 are sized and configured to fit within a shipment jar, such as shipment jar 120 shown in FIG. 12. With this sizing, valve support 160 does not interfere with the seal of the jar 120. Additionally, the size and shape of valve support 160 allows for easy insertion and removal of the valve support from the jar 120, such that sufficient clearance is provided to allow for insertion and removal of the valve support without damage to the valve support and/or replacement heart valve 100, while also partially or fully limiting motion of the valve support 160 within the jar during transportation.

Figure 5:
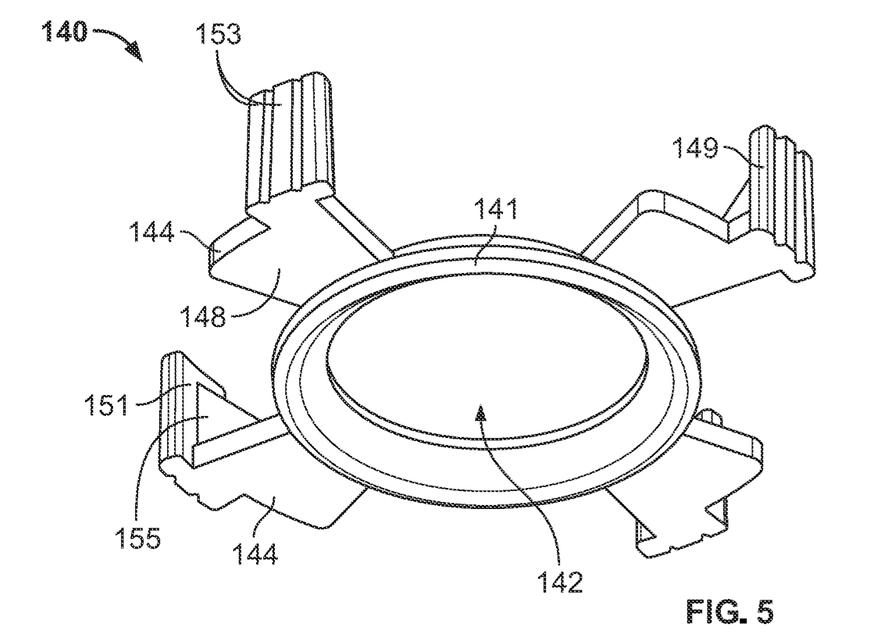
FIG. 5 is a perspective side view of the ring component of the packaging assembly of FIGS. 2-4.
Figure 6:
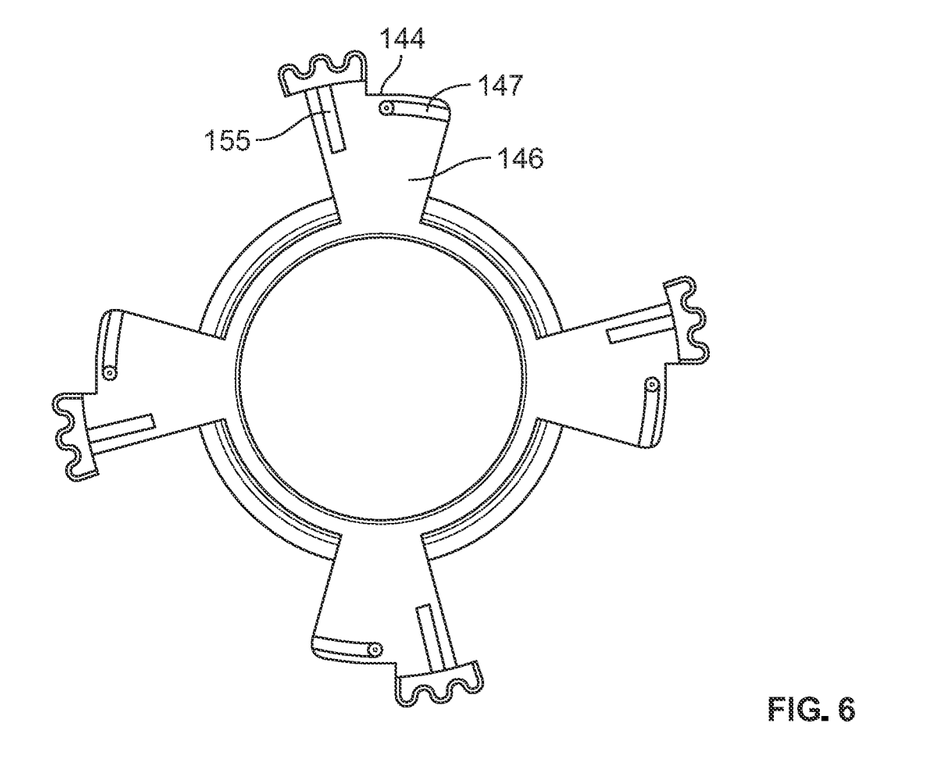
FIG. 6 is a top view of the ring component of FIG. 5.

Ring 140 is described in further detail with reference to FIGS. 5-7. Ring 140 includes body 141 having an annular shape and defining opening 142 therethrough. Ring 140 removably attaches to valve support 160 with an attachment mechanism. In the illustrated embodiment, the attachment mechanism is in the form of four spaced apart locking tabs 144 extending radially outward from body 141 and spaced around the circumference of the ring. As in the illustrated embodiment, locking tabs 144 may be evenly spaced apart around the circumference of the body 141. Locking tabs 144 may be spaced about 90 degrees from adjacent locking tabs, as shown in FIG. 6. In other examples, the locking tabs may be arranged at different intervals around body 141 relative to one another. In FIGS. 5 and 6, ring 140 includes four locking tabs 144, although in other examples there may be more or fewer the locking tabs.

Figure 7:
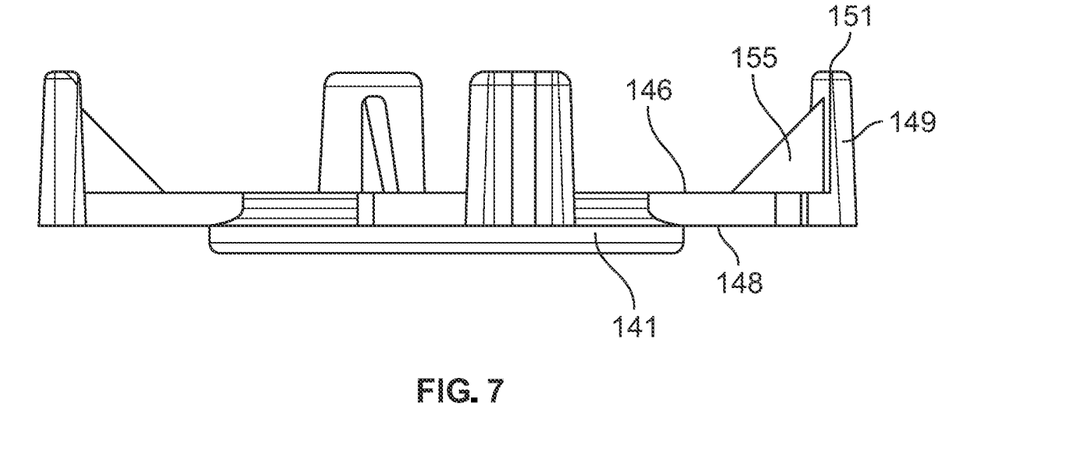
FIG. 7 is a side view of the ring component of FIG. 5.

As shown in FIG. 7, each locking tab 144 includes a proximal surface 146 and opposing distal surface 148. Proximal and distal surfaces 146, 148 may be substantially planar. Locking tab 144 includes extension 149 that extends the furthest radially outward of the locking tab 144. Extension 149 has a generally rectangular shape with the length extending in the proximal-distal direction. Although, in other examples the extensions may be trapezoidal, round, triangular and are not limited to the shape shown in the figures. Extension 149 may also include ridges 153 on an outer surface thereof. In the illustrated embodiment, ridges 153 extend in the proximal-distal direction and may facilitate a user in readily gripping the extensions 149 to manipulate (e.g. rotating) the ring 140. It should be understood that additional or alternative texturizations may be provided to assist with manipulation and/or gripping of portions of ring 140. A ramp 155 may be positioned between extension 149 and body 141, and in the illustrated embodiment is connected to inner surface 151 of extension 149 and proximal surface 146 to provide structural support for extension 149. Ramp 155 has a substantially triangular shape from the side view as shown in FIGS. 5 and 7, which provides support to the extension 149. Proximal surface 146 also includes a groove 147 for receiving a corresponding projection of the valve support to form a snap fit connection with the valve support.

Locking tabs 144 may allow ring 140 to be moved via rotation from an unlocked position to a locked position in which ring 140 is rotationally and axially locked with valve support 160. Such connection is described in further detail below in connection with additional descriptions of FIGS. 2-4. Extensions 149 may provide a hard stop feature to prevent over-rotation of ring 140 within valve support 160.

Figure 8:
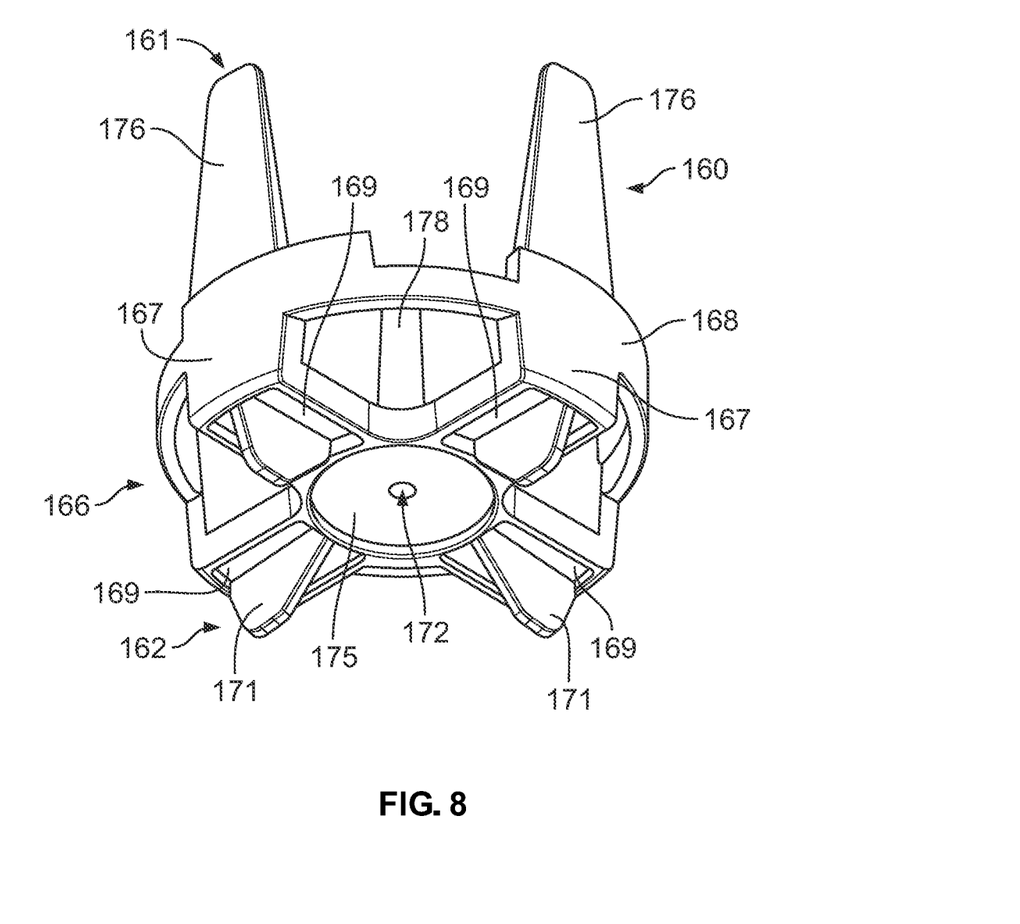
FIG. 8 is a perspective bottom view of the valve support component of the packaging assembly of FIGS. 2-4.
Figure 9:
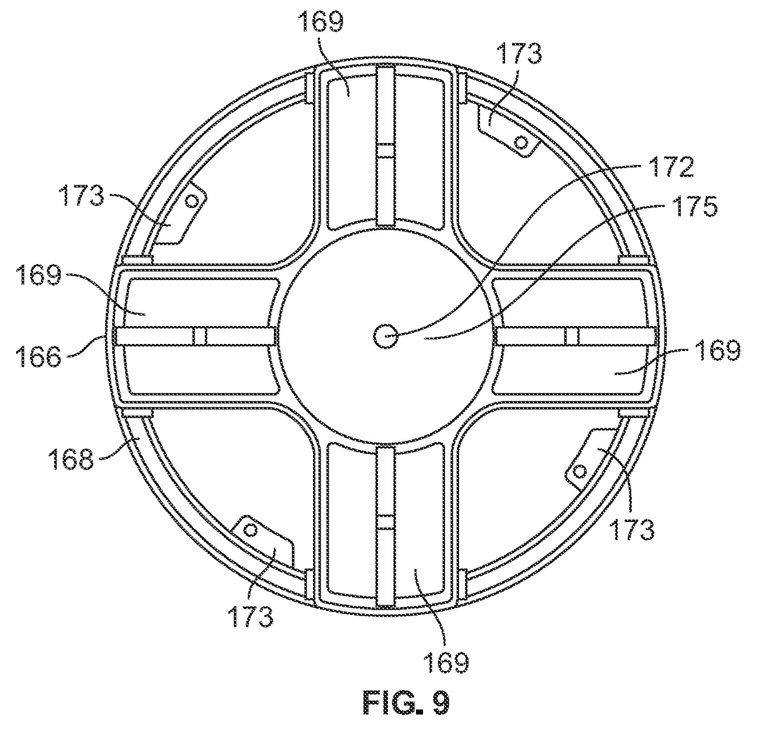
FIG. 9 is a top view of the valve support component of FIG. 8.

Valve support 160 is described in further detail with reference to FIGS. 8-11. Valve support 160 has proximal end 161 and distal end 162 and includes base 166 near the proximal end. Base 166 includes outer rim 168 with four platforms 169 extending proximally from rim 168 and connected to the rim by a respective arm 167, platforms which extend across rim 168 to form a "x'- or "cross"-shape such that outer rim 168 is radially outward of platforms 169, as shown in FIGS. 8 and 9. A proximal surface of base 166 may include ridges along the surface to provide rigidity to the base. Platforms 169 connect to each other at central portion 175. The central portion 175 may be generally circular and may define a central opening 172 for receiving a pin 182 (shown in FIG. 4) and/or a mandrel or other alignment tool therethrough. Each platform 169 may have a respective rib 171 extending proximally from a proximal surface of base 166, and the ribs 171 may be positioned on respective platforms 169 between the outer diameter of the base and central portion 175. Ribs 171 may provide locations for the user to grasp the valve support 160 to lift the valve support out of the jar, for example without sacrificing sterility of the replacement heart valve or contacting more sensitive components.

Figure 10:
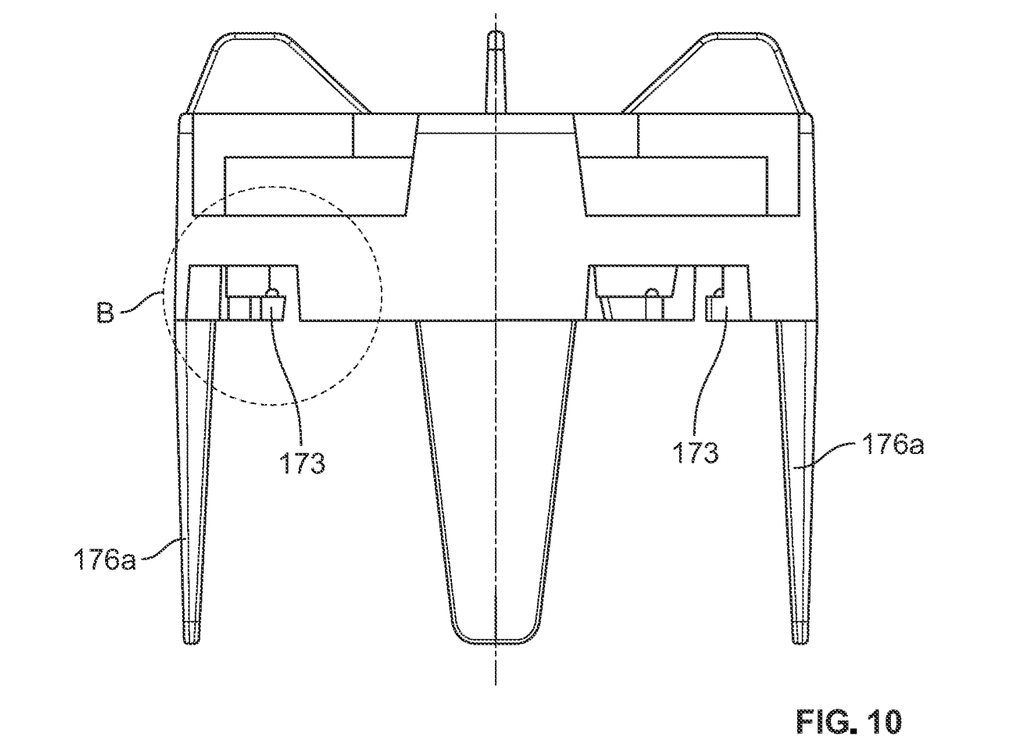
FIG. 10 is a side view of the valve support component of FIG. 8.
Figure 11:
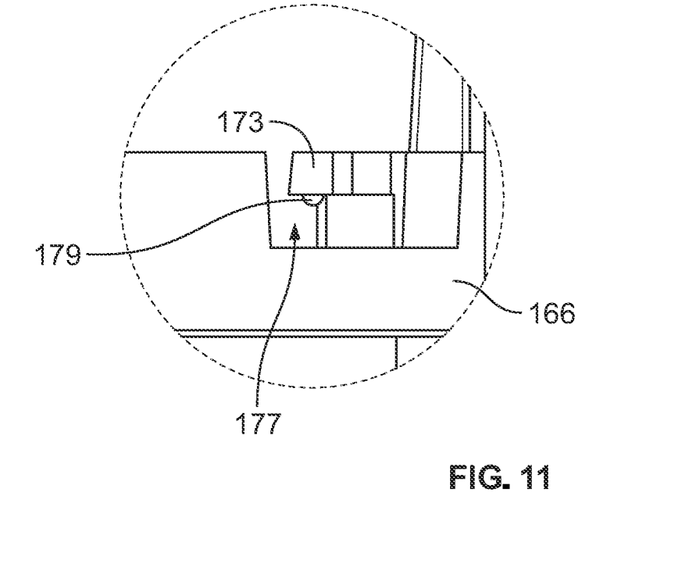
FIG. 11 is an enlarged view of Detail B of FIG. 10.

Base 166 includes a plurality of fins 176 extending distally from outer rim 168 which align with a respective one of the plurality of arms 167. Each fin 176 includes lateral side walls which taper inward in the proximal-distal direction such that the fin has a generally trapezoidal shape. Fins 176 are designed to provide rigidity to valve support 160 and protect replacement heart valve 100 from the walls of the jar 120 during shipment. In this regard, the fins 176 may be any shape including round, rectangular, triangular, which would enable the fins to provide rigidity to the structure. In this embodiment, there are four fins 176 equally spaced around the circumference of outer rim 168 of valve support 160 with the fins 176 being spaced about 90 degrees apart from adjacent fins. Accordingly, the four arms 167 are also spaced apart from adjacent arms about 90 degrees. As shown in FIG. 10, adjacent a side wall 176a of each fin 176 is ledge 173 projecting radially inward of outer rim 168 to define a groove 177 between ledge 173 and outer rim 168 for receiving a portion of locking tab 144. Further, ledge 173 includes projection 179 sized and shaped to engage groove 146 of locking tab 144 to form a snap fit connection. This connection rotationally and axially locks ring 140 to valve support 160. Ledge 173 and groove 177 are best shown in FIGS. 10 and 11. When locking tab 144 of ring 140 is positioned within the groove 177 of valve support 160, extension 149 may abut a side surface of ledge 173 to prevent further rotation of ring 140, as shown in FIG. 3.

With reference to FIG. 8, valve support 160 further includes cannulated rod 178 defining a central lumen (not shown) which aligns with central opening 172 of central portion 175 of base 166, the lumen configured to receive pin 182 of retention mechanism 180. When replacement heart valve 100 is packaged within packaging assembly 130, cannulated rod 178 is positioned extending through central opening 106 of the replacement heart valve 100, and also through an opening between the prosthetic leaflets disposed within support frame 105. Rod 178 has an exterior surface that is advantageously smooth to prevent abrasion or damage to the replacement heart valve, including abrasion to the prosthetic leaflets.

Packaging assembly 130 further includes retention mechanism 180, shown in FIGS. 2-4. As shown in FIG. 3, retention mechanism 180 of packaging assembly 130 includes pin 182, cap 186 for attaching to the pin 182 and sutures 190 for attaching the retention mechanism to the replacement heart valve 100. A first end of the sutures 190 is secured to cap 186 and a second end of each suture includes a loop to attach to attachment members 118 of the replacement heart valve 100. Retention mechanism 180 allows for secure attachment of replacement heart valve 100 within packaging assembly 130 during shipment, removal from shipment jar 120, and rinsing of the replacement heart valve.

As shown in FIG. 4, cannulated pin 182 includes a distal portion 183 having a first diameter which transitions to a proximal portion 184 having a second diameter at step 185, the second diameter being smaller than the first diameter. Proximal portion 184 is sized and configured to fit within an inner lumen (not shown) of cap 186. Cap 186 can be attached to pin 182 via a cooperating threaded engagement between an external surface of proximal portion 184 and an inner surface of cap 186 (not shown) which defines the lumen.

Step 185 forms a shoulder to control the position of cap 186 on pin 182. The outer surface of cap 186 is threaded for attaching the delivery system 200 to the retention mechanism 180 of packaging assembly 130. Cap 186 includes a portion, either monolithic with the cap or attached thereto, that enables sutures 190 to be threaded therethrough. In the illustrated embodiment, cap 186 includes collar 187 having a plurality of openings (not shown) for receiving suture strands 190 such that a first end of the suture can be secured through the openings thereby securing the sutures to the cap. The cap and collar may be monolithic, e.g. constructed from a single piece, or they may be separate pieces mechanically joined together thereafter. A second end of the suture 190 is looped over a respective one of the plurality of attachment members 118 on a proximal end of replacement heart valve 100 which causes tension on suture strands 190. In one example, there may be twelve suture strands 190 connected to pin 182 and attachment members 118. In order to achieve tension on suture strands 190, pin 182 is designed to have a height sufficient to create such tension when the suture strands are positioned through the retaining elements and the cap. Pin 182 can be positioned within rod 178 to the desired height based on the size of the replacement heart valve. In order to maintain pin 182 within the lumen of rod 178, the pin 182 is structured to facilitate to an interference fit. In one example, the pin may be tapered such that the outer diameter of the pin is greater than the inner diameter of the rod 178. This enables the pin 182 to be inserted to a specified depth and kept in place. Alternatively, the pin 182 could include threads for threaded engagement with the internally threaded rod, or the pin and/or lumen of the rod could be stepped and the engagement could be achieved through a friction fit of the stepped configuration. Crimp members 192 may be provided around at least a portion of each suture strand 190 to form the loop at the end of the suture. Crimp members 192 may help to prevent possible hooking onto other features of the valve holder assembly. In some cases, the crimps or coils on sutures 405 are secured in place by an adhesive, which can help maintain tension and avoid inadvertent separation of the sutures 405. Although described herein as suture, the material can alternatively be wire or another flexible member capable of tensioning the replacement heart valve 100.

To assemble packaging assembly 130 to its assembled configuration, shown in FIGS. 2-4, in which ring 140 and valve support 160 are locked together and replacement heart valve 100 is positioned within and secured to ring 140, ring 140 is positioned within valve support 160 and rotated in a first direction such that locking tabs 144 slide into the grooves defined by ledges 173 and mechanically lock to valve support 160 via the snap fit connection. Pin 182 is positioned within a proximal portion of cannulated rod 178 with proximal portion 184 of pin 182 extending beyond rod 178. Body 141 of ring 140 is positioned so that it securely fits around the waist defined by central portion 103 of the hour-glass shaped anchor assembly 101 of replacement heart valve 100 (FIG. 1). Replacement heart valve 100 is positioned with ventricular anchor 104 adjacent base 166 of valve support 160. This allows for a circumferentially snug and secure fit prevents movement of the replacement heart valve 100 within the packaging assembly 130. Pin 182 extends coaxial with a longitudinal axis of replacement heart valve 100. Cap 186 is attached to pin 182 with suture strands 190 looped through the openings of cap 186. For ease of assembly, suture strands 190 can be looped through the openings of cap 186 prior to attachment of the cap 186 with the valve support 160 and ring 140 structure. The loops of the suture strands 190 are attached to attachment members 118 of atrial anchor 102 of replacement heart valve 100 thereby tensioning suture strands 190. The tension on suture strands 190 prevents inadvertent release of the suture loops on attachment members 118 and also constrains the valve fully in the axial direction. Further, the tension of suture strands 190 also holds cap 186 against the shoulder of pin 182. Thus, the positioning of body 141 of ring 140 around the valve together with the tension of suture strands 190 provide for full axial and circumferential securement of replacement heart valve 100.

Figure 12:
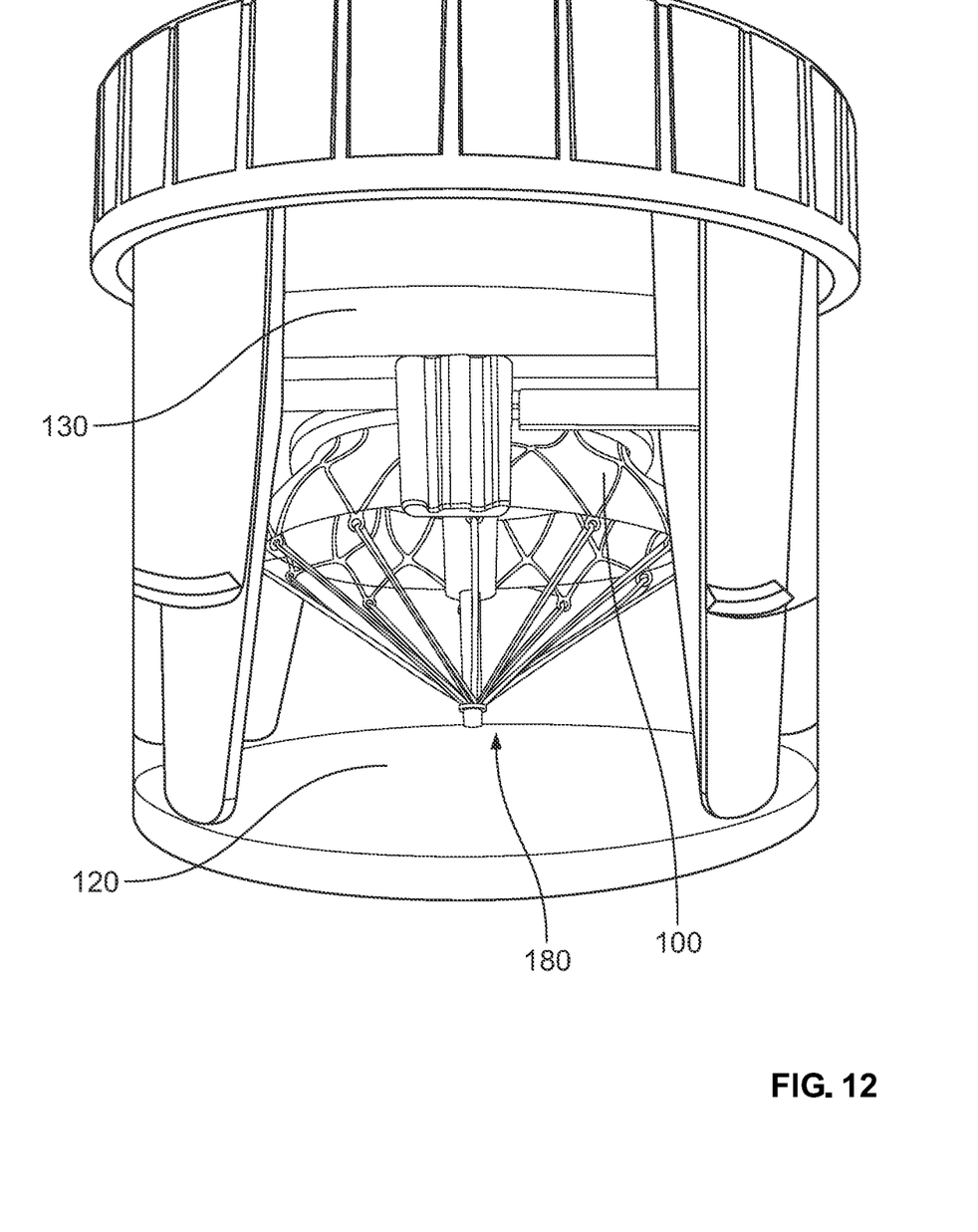
FIGS. 12 and 13 are photographs of the replacement heart valve and packaging assembly of FIGS. 2-3 in conjunction with a shipment jar.

The assembled configuration of packaging assembly 130 is in a final configuration for insertion into a shipment jar 120, shown in FIG. 12, which then is filled with shipment fluid. In this configuration, ventricular anchor 104 of replacement heart valve 100 faces toward the open end of jar 120, and atrial anchor 102 of replacement heart valve 100 faces toward the bottom or closed end of jar 120. During travel, replacement heart valve 100 is securely disposed within packaging assembly 130 such that it does not move around within shipment jar 120 and is prevented from hitting the walls of the jar. This, in turn, substantially reduces the risk of damage to the replacement heart valve during shipment.

Figure 13:
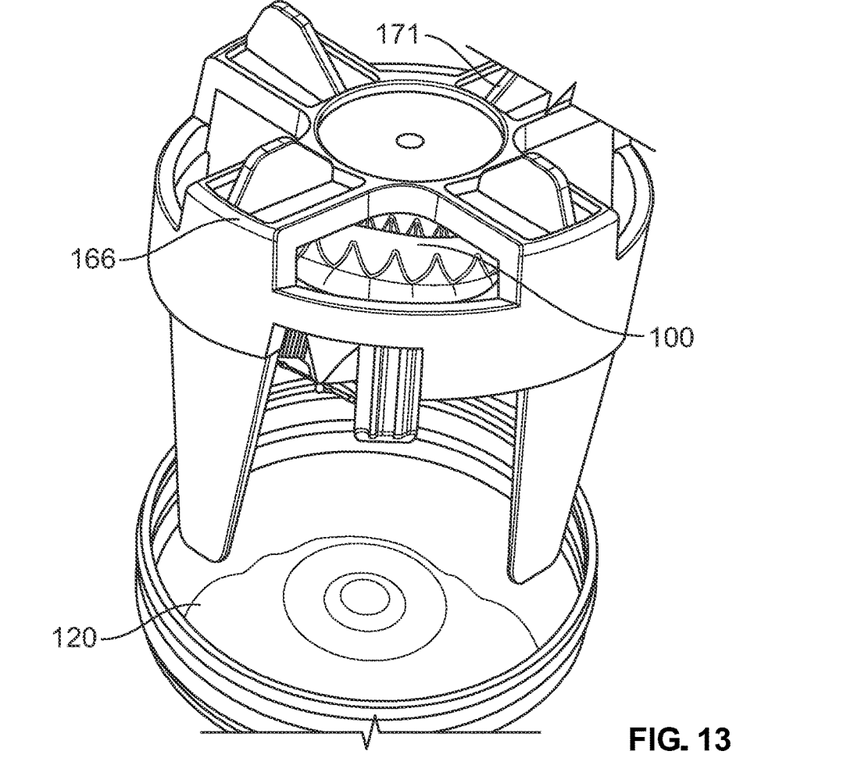
Figure 14:
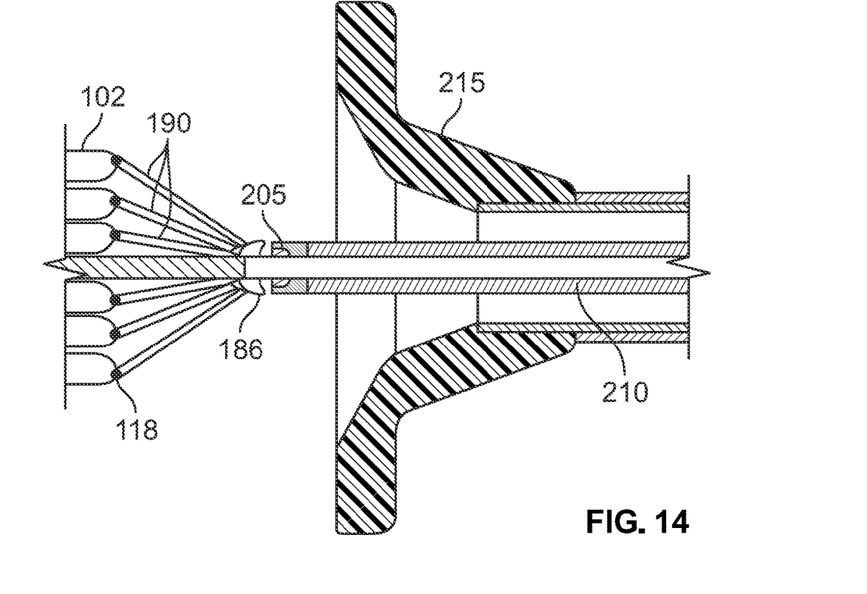
FIG. 14 is a perspective side view of an atrial anchor of a replacement heart valve and delivery system.
Figure 15:
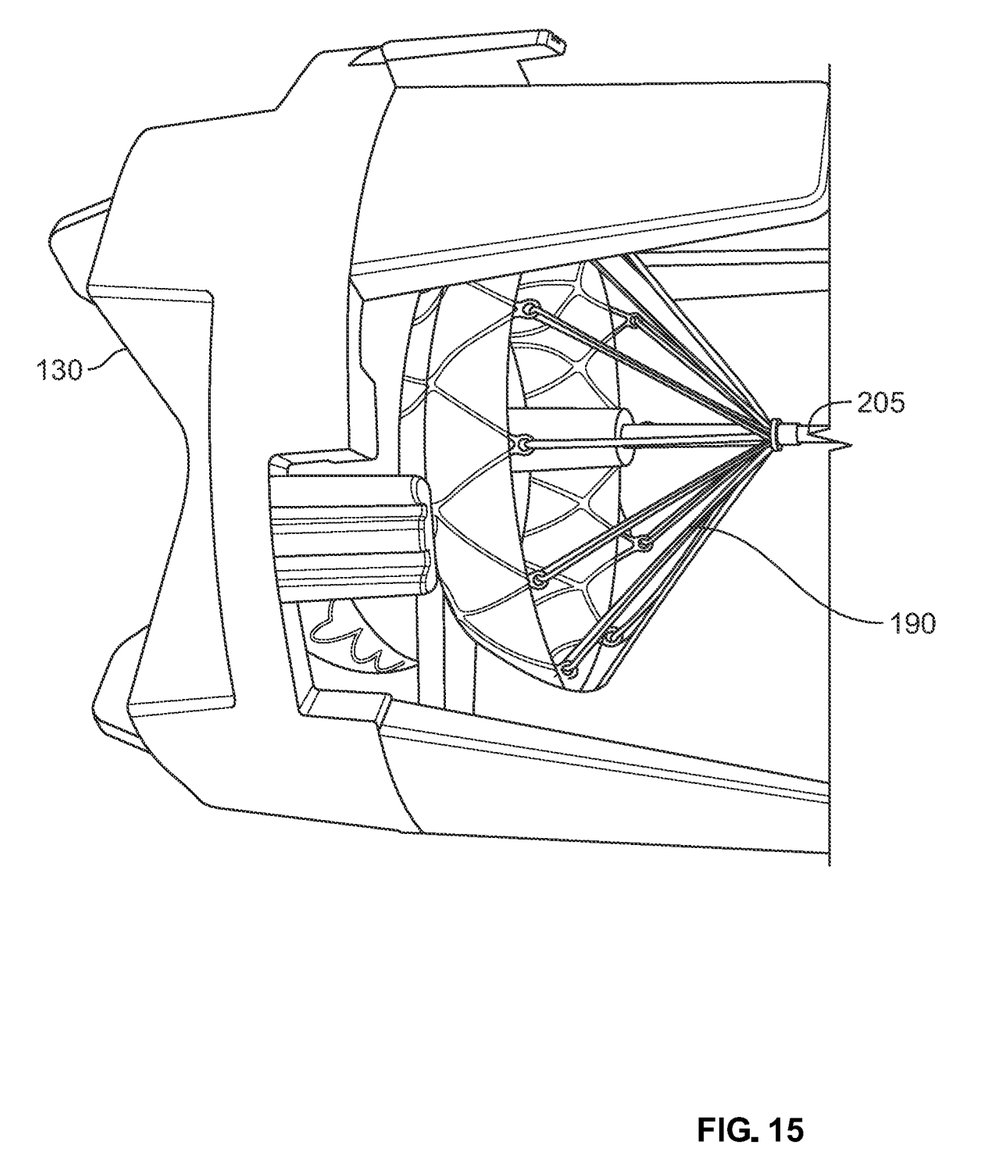
FIG. 15 is a photograph of the packaging assembly and replacement heart valve of FIGS. 2 and 3.

For preparing replacement heart valve 100 for implantation within a patient, after shipment, packaging assembly 130 is lifted from the shipment jar 120. The user holds onto at least one rib 171 and lifts the packaging assembly 130 from the shipment jar 120, as shown in FIG. 13. Packaging assembly 130 may then be placed into one or more bowls of rinsing materials, such as sterile saline. Preferably, packaging assembly 130 may be placed into three separate sterilizing bowls in successive steps. With the delivery system 200 assembled, packaging assembly 130 can be loaded onto delivery system 200. A mandrel can be inserted through rod 178 and pin 182 to align retention mechanism 180 with the receiving component of the delivery system 200 when the replacement heart valve is being connected to the delivery system 200 to maintain the coaxial nature of the cap 186 and receiving portion 205. Packaging assembly 130 is threadably attached to delivery system 200 by threading cap 186 of retention mechanism 180 onto receiving portion 205 of suture catheter 210, as shown in FIGS. 14 and 15. Exemplary methods of attaching the delivery system to the replacement heart valve are described in U.S. Patent Publication No. 2018/0092744 filed on Oct. 4, 2017 and entitled Systems and Methods for Delivering and Deploying an Artificial Heart Valve Within The Mitral Annulus," the disclosure of which is hereby incorporated by reference herein.

As cap 186 is pulled into the delivery system 200, the sutures 190 are also pulled within loading funnel 215 of delivery system 200 and replacement heart valve 100 moves into a partially collapsed configuration in which at least a portion of atrial anchor 102 is positioned within the loading funnel 215. Packaging assembly 130 can be dissembled and removed. To do so, valve support 160 is rotated to overcome the snap fit and to release ring 140 from valve support 160. Valve support 160 can be removed distally, e.g. in a direction away from the delivery system 200. Upon further collapse of the ventricular anchor 104 of replacement heart valve 100, a maximum diameter of the replacement heart valve 100, including the ventricular anchor 104, is less than the inner diameter of the ring. At that point, ring 140 can be pulled distally and away from the delivery system 200 to remove the ring component.

Figure 16:
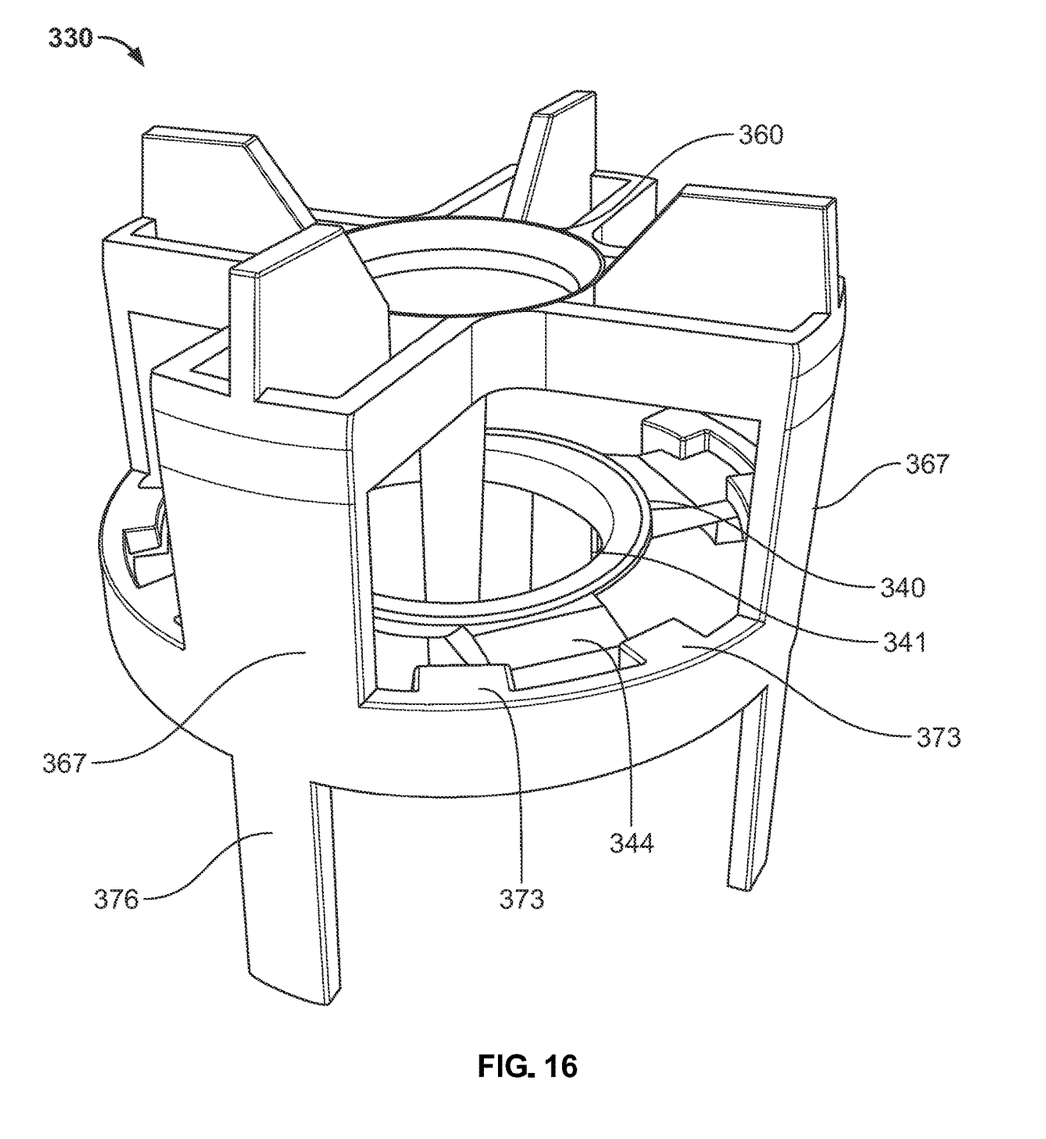
FIG. 16 is a photograph of a packaging assembly according to another aspect of the present disclosure.

FIG. 16 shows packaging assembly 330 according to another aspect of the present disclosure. Packaging assembly 330 is substantially similar to packaging assembly 130, such that only the differences will be discussed. In this aspect, ring 340 includes a plurality of locking tabs 344 for snap fit engagement with valve support 360 to prevent rotation and axial movement of the ring relative to the valve support. Locking tabs 344 project radially outward from body 341 of ring 340 and snaps into a groove (not shown) defined by two spaced apart ledges 373 such that there are two ledges 373 positioned between adjacent arms 367. Further, in this embodiment, fins 376 are substantially rectangular in shape. Packaging assembly 330 functions in substantially the same manner as packaging assembly 130, described above.

The packaging assemblies of the present disclosure are designed to securely hold a replacement heart valve within the packaging assembly during shipment in a shipment jar container and allow for pre-tensioning of the replacement valve such that the replacement valve is tensioned in the packaging. This allows the replacement heart valve to be rinsed and attached to the delivery device while in a protected configuration securely within the packaging assembly. The packaging assemblies further allow pre-tensioning of the replacement heart valve to the retention mechanism of the packaging assembly so that the assembly is tensioned when attached to the delivery device which enables a more efficient implantation preparation. Additionally, should the operator decide that a different catheter is needed, for example, if a different valve size is needed based on the anatomy of the patient, the devices described herein allow for quicker changeability amongst delivery devices.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A packaging assembly for packaging a replacement heart valve, the packaging assembly comprising:
    a valve support having a base;
    a ring positioned within the valve support and configured to fit around a circumference of the replacement heart valve; and
    a retention mechanism including a pin extending through a lumen of the valve support and a plurality of sutures attached to the pin, wherein the plurality of sutures are configured to be attached to the replacement heart valve.

2. The packaging assembly of claim 1, wherein the packaging assembly has an unlocked configuration, in which the ring and the valve support are detached, and a locked configuration, in which the ring and the valve support are locked together.

3. The packaging assembly of claim 2, wherein in the locked configuration, the ring and the valve support are rotationally and axially locked to one another.

4. The packaging assembly of claim 3, wherein the packaging assembly transitions between the unlocked and locked configurations by rotation of at least one of the ring and the valve support relative to the other.

5. The packaging assembly of claim 3, wherein in the locked configuration, the ring and the valve support are locked together by a snap-fit connection.

6. The packaging assembly of claim 1, wherein the retention mechanism further includes a cap attached to the pin for securing the plurality of sutures.

7. The packaging assembly of claim 6, wherein the cap includes a plurality of openings, each opening is configured to receive at least one suture.

8. The packaging assembly of claim 7, wherein an outer surface of the cap is threaded for threaded engagement with a delivery system.

9. The packaging assembly of claim 1, wherein the ring includes an annular body and at least one locking tab extending radially outward of the body.

10. The packaging assembly of claim 9, wherein the valve support includes a ledge projecting radially inward from the base to define a groove for receiving a respective one of the at least one locking tab.

11. The packaging assembly of claim 10, wherein each of the locking tabs includes an extension extending proximally from a proximal surface of the locking tab.

12. The packaging assembly of claim 11, a side surface of each extension is configured to abut a side surface of the ledge to prevent over rotation of the ring.

13. A system for heart valve repair comprising:
    a replacement heart valve;
    a packaging assembly for storing the replacement heart valve, the packaging assembly including:
    a valve support having a base for holding the replacement heart valve;
    a ring positioned within the valve support and configured to fit around a circumference of the replacement heart valve;
    a retention mechanism including a cap and plurality of sutures configured to be attached to the cap and to the replacement heart,
    the packaging assembly having a locked configuration in which the ring and the valve support are locked together and the sutures tension the replacement heart valve.

14. The system of claim 13, wherein the replacement heart valve includes a plurality of attachment members for receiving the sutures of the retention mechanism.

15. The system of claim 13, wherein the replacement heart valve includes an anchor assembly having an atrial anchor and a ventricular anchor, the atrial anchor including a plurality of attachment members in the form of pins for receiving the suture of the retention mechanism.

16. The system of claim 15, wherein the cap of the retention mechanism includes a plurality of openings for receiving the suture, such that the suture extends between a respective one of the plurality of openings of the cap and a respective one of the plurality of attachment members.

17. The packaging assembly of claim 13, wherein the ring includes an annular body and at least one locking tab extending radially outward of the body.

18. The packaging assembly of claim 13, wherein the valve support includes a ledge projecting radially inward from the base and defining a groove for receiving a respective one of the at least one locking tab.

19. The packaging assembly of claim 18, wherein each of the locking tabs includes an extension extending proximally from a proximal surface of the locking tab, a side surface of each extension is configured to abut a side surface of the ledge to prevent over rotation of the ring.

20. A system for heart valve repair comprising:
a packaging assembly for storing a replacement heart valve, the packaging assembly including:
a valve support having a base for holding the replacement heart valve;
a ring positioned within the valve support and configured to fit around a circumference of the replacement heart valve;
a retention mechanism including a cap and plurality of sutures configured to be attached to the cap and to the replacement heart,
the packaging assembly having a locked configuration in which the ring and the valve support are locked together and the sutures tension the replacement heart valve;
a shipment jar for receiving the packaging assembly.

* * * * *